(12) United States Patent
Focke et al.

(10) Patent No.: US 7,275,438 B2
(45) Date of Patent: Oct. 2, 2007

(54) METHOD AND DEVICE FOR RECOGNITION OF A TEAR-OFF STRIP ON A MATERIAL WEB

(75) Inventors: Heinz Focke, deceased, late of Verden (DE); by Doris Focke, legal representative, Verden (DE); by Jürgen Focke, legal representative, Verden (DE); Michael Czarnotta, Bremen (DE)

(73) Assignee: Focke & Co. (GmbH & Co. KG), Verden (DE)

( * ) Notice: Subject to any disclaimer, the term of this patent is extended or adjusted under 35 U.S.C. 154(b) by 222 days.

(21) Appl. No.: 10/529,470

(22) PCT Filed: Oct. 2, 2003

(86) PCT No.: PCT/EP03/10961

§ 371 (c)(1),
(2), (4) Date: Mar. 28, 2005

(87) PCT Pub. No.: WO2004/033305

PCT Pub. Date: Apr. 22, 2004

(65) Prior Publication Data

US 2006/0077758 A1 Apr. 13, 2006

(30) Foreign Application Priority Data

Oct. 4, 2002 (DE) ................................ 102 46 437

(51) Int. Cl.
*G01N 29/265* (2006.01)
*B65H 19/16* (2006.01)

(52) U.S. Cl. ............................ 73/617; 73/618; 73/628; 250/559.12

(58) Field of Classification Search .................. 73/617, 73/609, 590, 597, 602, 596–600, 618, 628; 53/462, 207; 250/559.12
See application file for complete search history.

(56) References Cited

U.S. PATENT DOCUMENTS

| 4,363,032 | A | | 12/1982 | Kimoto |
| 4,682,038 | A | | 7/1987 | Focke |
| 4,901,577 | A | | 2/1990 | Roberts |
| 5,929,337 | A | * | 7/1999 | Collins et al. ................. 73/597 |
| 5,966,904 | A | | 10/1999 | Peters |
| 6,038,836 | A | * | 3/2000 | Focke et al. ................... 53/462 |
| 6,125,708 | A | * | 10/2000 | Wang et al. ............. 73/862.49 |
| 6,308,492 | B1 | * | 10/2001 | Focke et al. ................... 53/55 |

(Continued)

FOREIGN PATENT DOCUMENTS

DE  30 42 106 C2  2/1988

(Continued)

*Primary Examiner*—Hezron Williams
*Assistant Examiner*—Jacques M. Saint-Surin
(74) *Attorney, Agent, or Firm*—Sughrue Mion pllc.

(57) ABSTRACT

In order to check a material web (12), in particular a film web, with regard to the correct arrangement of a tear-off strip (11) extending in the longitudinal direction of the material web (12), ultrasonic transmitters are used, specifically an ultrasonic transmitter (11) on the one hand and an ultrasonic receiver (19) on the other hand. The sensors are arranged on opposite sides of the material web (12) in such a way that, if appropriate, focused ultrasonic waves are aimed specifically at the region of the tear-off strip (11). If a tear-off strip (11) is missing, an appropriate signal is generated by the ultrasonic receiver (19).

14 Claims, 4 Drawing Sheets

U.S. PATENT DOCUMENTS

| | | | |
|---|---|---|---|
| 6,993,972 B2 * | 2/2006 | Basir et al. | 73/625 |
| 7,067,833 B2 * | 6/2006 | Ramm | 250/559.12 |
| 7,107,852 B2 * | 9/2006 | Hutchins et al. | 73/598 |
| 2002/0000458 A1 | 1/2002 | Ludwig | |
| 2002/0065181 A1 | 5/2002 | Focke et al. | |
| 2004/0113805 A1 * | 6/2004 | Fardin et al. | 340/686.2 |

FOREIGN PATENT DOCUMENTS

| | | |
|---|---|---|
| DE | 33 41 539 C2 | 3/1991 |
| DE | 195 16 868 A1 | 11/1996 |
| DE | 196 48 360 A1 | 6/1998 |
| DE | 696 20 361 T2 | 11/2002 |
| EP | 779 219 | 6/1997 |
| EP | 1 209 083 A2 | 5/2002 |
| GB | 1 206 441 | 9/1970 |

* cited by examiner

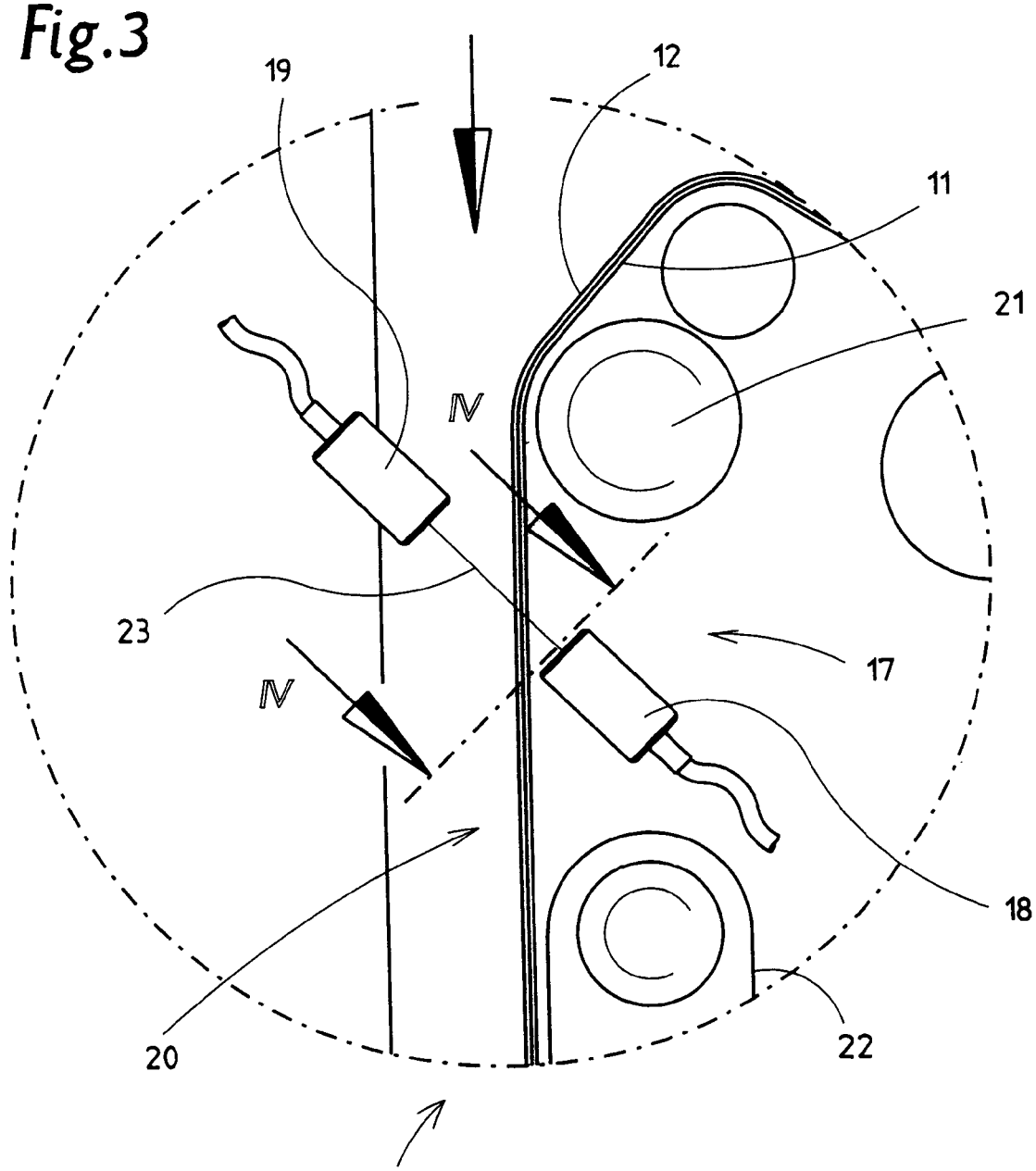
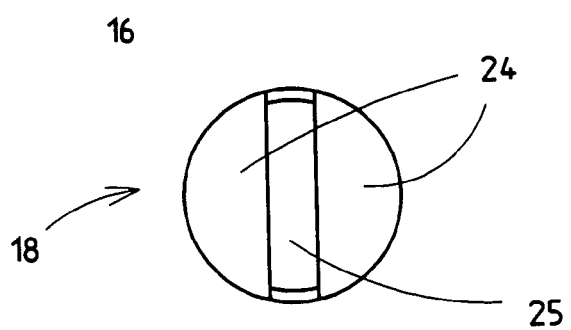

METHOD AND DEVICE FOR RECOGNITION OF A TEAR-OFF STRIP ON A MATERIAL WEB

BRIEF DESCRIPTION OF THE INVENTION

The invention relates to a method for detecting, with the aid of sensors, a tear-off strip or tear-off thread applied to a material or film web. Furthermore, the invention relates to an apparatus for implementing the method.

During the production of packs with external wrapping made of film, in particular cigarette packs or cigarette multi-packs, the film is provided with a tear-off thread or a tear-off strip, in order to make it easier to remove the outer wrapping when the pack is put into use. The tear-off strip is applied to a continuous material web or film web and joined to the latter. After that, the blanks for wrapping the pack are severed from the web (EP 1 209 083).

The presence and the correct positioning of the tear-off strip on the material web are checked (continuously). For this purpose, in the prior art, optoelectronic and capacitive sensors are used, which are aimed at the material web in the region of the tear-off strip. The sensors react to markings on the tear-off strip which can be registered optically.

The optoelectronic registration of the tear-off strip or tear-off thread fails if there is no adequate optical contrast or if, for example, the material web is entirely or partly printed or metallized.

SUMMARY OF THE INVENTION

The invention is based on the object of detecting a tear-off thread or tear-off strip on a material web or film web without contact, specifically irrespective of any optical contrast.

In order to achieve this object, the method according to the invention is defined by the following features:
  a) the sensors for detecting the tear-off strip or tear-off thread are ultrasonic transmitters, on the one hand, and ultrasonic receivers, on the other hand, which are positioned on different sides of the material web,
  b) ultrasonic transmitter and ultrasonic receiver are aimed substantially exactly at the tear-off thread or tear-off strip,
  c) the ultrasonic transmitter is constructed in such a way that a lobe or response curve generated by the latter corresponds approximately to the width of the tear-off strip,
  d) the ultrasonic receiver is connected to an evaluation unit which reacts to changes in the intensity of the waves picked up.

Testing thin-walled workpieces by means of ultrasound is basically known. Hitherto, this detection method has been used in double-sheet control, that is to say in checking (equally sized) sheets of thin material, in particular paper, with regard to any double-layer nature.

The invention is based on the finding that, by means of ultrasonic sensors, the position of a narrow material strip, mainly of a tear-off strip or tear-off thread, on a continuous thin material web is possible, specifically during continuous testing. For this purpose, the transmitter and receiver are aimed specifically at the tear-off strip or tear-off thread in the exact position of the same. The material web having tear-off strips or tear-off threads is preferably moved continuously past transmitter and receiver, in such a way that the ultrasonic waves are aimed in a concentrated manner at the region of the tear-off strip or tear-off thread.

In this case, according to the findings of the invention, the response curve of the receiver can deviate (slightly) from the width of the tear-off strip, as long as a measurable difference is provided by the receiver when picking up the ultrasonic waves in order to differentiate between an existing tear-off strip and a missing tear-off strip. The dimensioning of the lobe or response curve can then be determined by the intensity of the transmitter. One special feature, however, is the configuration according to the invention of the transmitter in such a way that the latter has an aperture stop that reduces the free transmitter area and which has the effect of a specific, limited response curve.

Further details of the invention relate to the expedient arrangement of the testing elements within a (packaging) machine.

Further special features of the invention will be explained in more detail below using exemplary applications and embodiments.

BRIEF DESCRIPTION OF THE DRAWING

FIG. 3 shows a further enlarged detail III from FIG. 2, FIG. 4 shows a detail of an ultrasonic transmitter, namely a plan view IV-IV of FIG. 3.

DETAILED DESCRIPTION OF A PREFERRED EMBODIMENT

Figure 1:
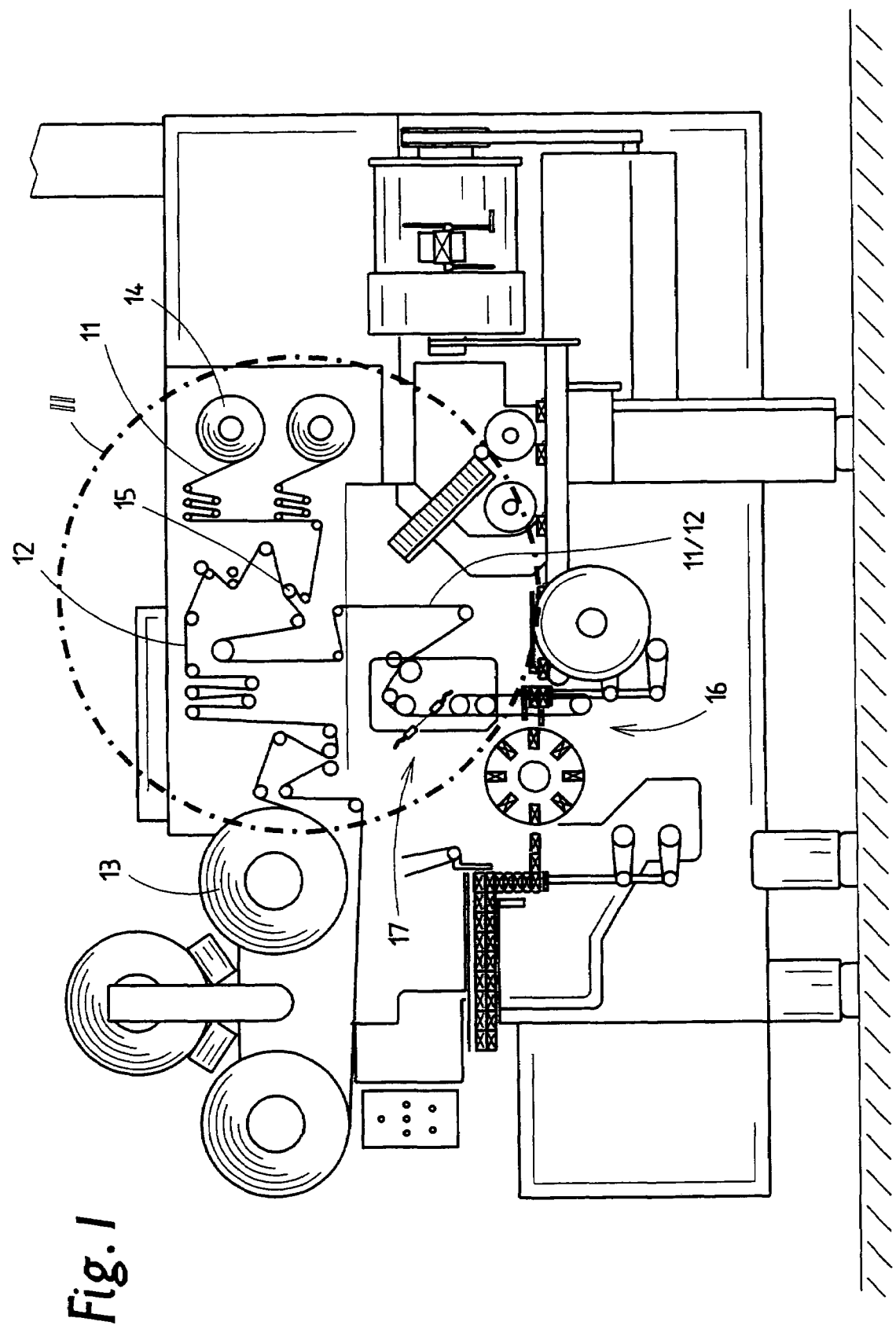
FIG. 1 shows a packaging machine for wrapping (cigarette) packs in a film wrapper, in a schematic side view.
Figure 2:
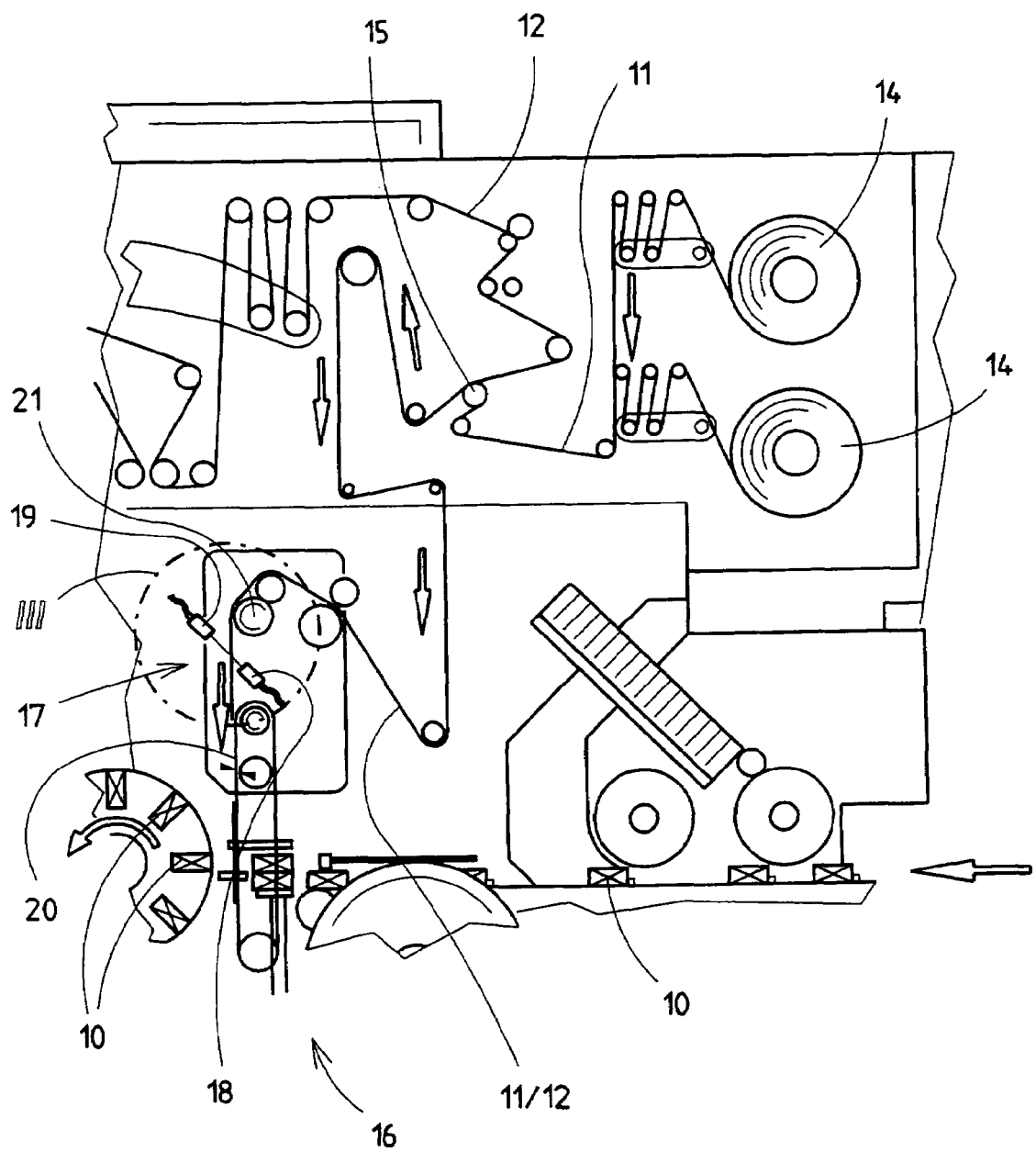
FIG. 2 shows a detail II from the view according to FIG. 1 on an enlarged scale.

The exemplary embodiment shown concerns the production of box-like packs 10, specifically cigarette packs, which are provided with an outer wrapper made of film. This has a tear-off strip 11 or a tear-off thread, which is positioned at a specific point in order to make the opening operation of the closed pack possible.

The tear-off strip 11 is applied to a continuous material web 12 of film for this purpose. The latter is drawn continuously from a reel 13. The continuous tear-off strip 11 is drawn from a strip reel 14 and, during transport in the same direction, is pressed onto the material web 12 and joined to the latter by a pressure roll 15. The unit comprising material web 12 with tear-off strip 11 is then supplied to a blank-cutting unit 16. In the region of the latter, individual blanks—with tear-off strip 11—are severed from the material web 12 and respectively folded around a pack 10. The apparatus for handling the tear-off strip 11, the material web 12 and for producing the blanks expediently corresponds to EP 1 209 083.

It is necessary to check whether the material web 12 is provided with a tear-off strip 11 and whether the latter is positioned correctly. A testing unit 17 is used for this purpose. This operates without contact on the basis of ultrasonic waves. An ultrasonic transmitter 18 and an ultrasonic receiver 19 are positioned on opposite sides of the material web 12. The ultrasonic transmitter 18 aims ultrasonic waves specifically at the material web 12, specifically in the region of the tear-off strip 11. The opposite ultrasonic receiver 19 picks up the sound waves. Transmitter, receiver and an evaluation unit connected to the receiver are constructed in such a way that any fluctuations in the intensity of the received ultrasonic waves are evaluated and findings relating to the presence or lack of a tear-off strip 11 can be obtained from this. The action of the testing unit 17 is such that, given the presence of a tear-off strip 11, attenuation by the tear-off strip 11 of the sound waves emitted occurs and, in the region of the ultrasonic receiver 19, leads to considerably reduced reception.

The testing unit 17 is positioned in the region of a vertical web section 20 of the material web 12, specifically following a deflection roll 21 immediately above or in the conveying direction upstream of the blank-cutting unit 16. In the present exemplary embodiment, the testing unit 17 is accordingly positioned immediately above a suction belt 22 for the transport of the material web 12 and the severed blanks in the region of the blank-cutting unit 16. It is a matter of carrying out the testing of the tear-off strip 11 as immediately as possible before the severing of the blank. The testing is advantageously after the last deflection roll 21.

Transmitter and receiver are arranged such that the ultrasonic waves are directed along an obliquely oriented axis 23 in an idealized manner. Accordingly, the ultrasonic waves are aimed at the material web 12 at an acute angle to the latter. The ultrasonic transmitter 18 is in this case located on the side of the tear-off strip 11, and the ultrasonic receiver 19 is located opposite on the side of the material web 12. The angle of the axis 23 with respect to the plane of the material web 12 is approximately between 70° and 45°. The distances of transmitter and receiver from the material web 12 are likewise different. The ultrasonic transmitter 18 is at a short distance, about 5 mm to 15 mm, from the material web 12, and the receiver 19 is at a greater distance of 15 mm to 65 mm. Alternatively, transmitter and receiver can be arranged transversely or at right angles with respect to the web 12.

The ultrasonic sensors are constructed in a particular way, so that a defined, limited lobe or response curve of the sound waves is produced, which is aimed exactly at the region of the tear-off strip 11. The defined response curve, approximately of the width of the tear-off strip 11, can be produced by an appropriate construction of the ultrasonic transmitter 18. In particular, the ultrasonic transmitter 18 can be provided on the outlet side with an aperture stop 24, which limits the emergence of the sound waves. In the exemplary embodiment shown in FIG. 4, the aperture stop 24 is formed in such a way that the ultrasonic transmitter 18 (of circular cross-section) has a central gap 25 running diametrically. This forms the outlet area for ultrasonic waves. The gap 25 extends in the direction of the tear-off strip 11. A focused region of the sound waves is aimed through the aperture stop 24 or the gap 25 by the ultrasonic transmitter 18 at the material web 12 in the region of the tear-off strip 11.

Figure 5:
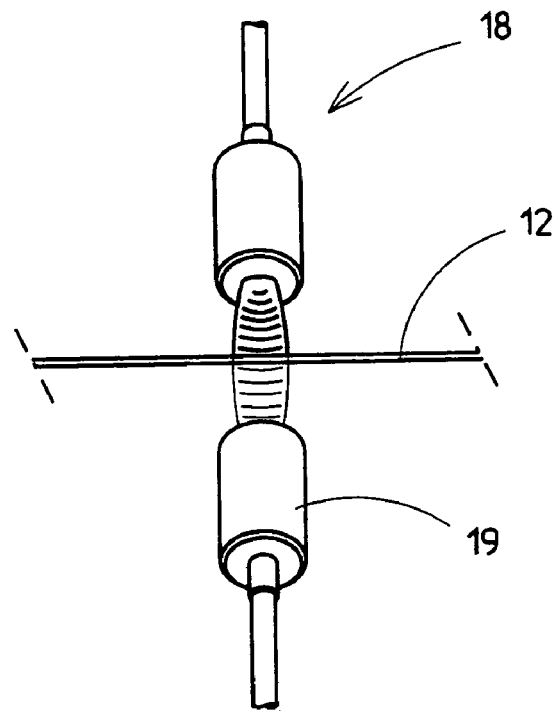
FIG. 5 shows the schematically illustrated mode of operation of ultrasonic transmitter and ultrasonic receiver when a tear-off strip is missing.
Figure 6:
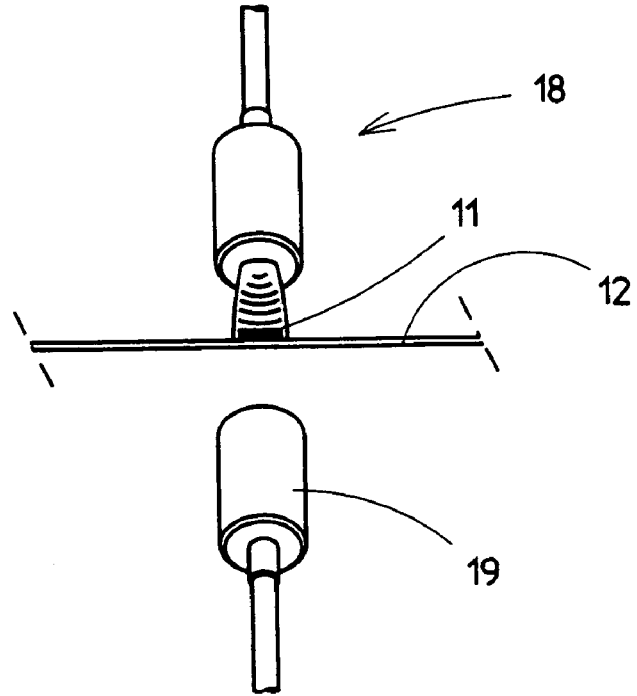
FIG. 6 shows a corresponding illustration with a correct tear-off strip.

The course of the "lobe" or the response curve of the ultrasonic waves is shown schematically in FIG. 5 and FIG. 6, FIG. 5 showing the case of a missing tear-off strip with sound waves passing largely unhindered through the material web 12. FIG. 6 is the illustration of the correctly formed material web 12 with tear-off strip 11. The sound waves originating from the ultrasonic transmitter 18 are absorbed completely or predominantly by the material web 12 with tear-off strip 11, so that the ultrasonic receiver 19 receives no sound waves or highly attenuated sound waves.

The evaluation unit (not shown) generates a signal when the material web is not correctly provided with a tear-off strip 11, with the effect of FIG. 5.

LIST OF DESIGNATIONS

10 Pack
11 Tear-off strip
12 Material web
13 Reel
14 Strip reel
15 Pressure roll
16 Blank-cutting unit
17 Testing unit
18 Ultrasonic transmitter
19 Ultrasonic receiver
20 Web section
21 Deflection roll
22 Suction belt
23 Axis
24 Aperture stop
25 Gap

The invention claimed is:

1. A method for detecting a tear-off strip (11) or a tear-off thread on a material web (12) with the aid of sensors comprising an ultrasonic transmitter and an ultrasonic receiver, said method comprising the steps of:
   a) positioning the ultrasonic transmitter (18) and the ultrasonic receiver (19) on opposite sides, respectively, of the material web (12),
   b) positioning the ultrasonic transmitter (18) and the ultrasonic receiver (19) such that the material web (12) conveyed between the ultrasonic transmitter (18) and the ultrasonic receiver (19) is registered by ultrasonic waves substantially exclusively in a region of the tear-off strip (11) or tear-off thread,
   c) constructing the ultrasonic transmitter (18) in such a way that a response curve generated by the ultrasonic transmitter corresponds approximately to a width of the tear-off strip (11) or thread, and
   d) connecting the ultrasonic receiver (19) to an evaluation unit which reacts to changes in the intensity of the waves picked up the ultrasonic receiver.

2. An apparatus for implementing the method as claimed in claim 1, a tear-off strip (11) or tear-off thread being laid continuously on a continuously conveyed material web (12) and joined to the material web, so that blanks can be severed from the web,
   said apparatus comprising;
   following a joining station of the material web (12) and the tear-off strip (11) or thread, a testing device, for detecting the tear-off strip (11) or thread, positioned in a fixed location; and
   means for moving the web past said testing device,
   the testing device comprising at least one ultrasonic transmitter (18) and at least one ultrasonic receiver (19),
   said ultrasonic transmitter (18) and said ultrasonic receiver (19) being positioned on opposite sides of the material web (12) in such a way that ultrasonic waves originating from the ultrasonic transmitter (18) strike the material web (12) substantially exclusively in a region of the tear-off strip (11) or thread, so that ultrasonic waves passing through the material web are picked up by the opposite ultrasonic receiver (19).

3. The apparatus as claimed in claim 2, characterized in that said ultrasonic transmitter (18) and said ultrasonic receiver (19) are positioned in a region of an upright section (20) of the material web (12), immediately above an upright suction belt (22) of a blank-cutting unit (16).

4. The apparatus as claimed in claim 2, characterized in that said ultrasonic transmitter (18) and said ultrasonic receiver (19) are oriented in an oblique position with respect to a plane of the material web (12).

5. The apparatus as claimed in claim 2, characterized in that the ultrasonic transmitter (18) is arranged underneath the ultrasonic receiver.

6. The apparatus as claimed in claim 2, characterized in that the ultrasonic transmitter (18) is provided with a limiting means on an outlet side thereof in order to influence the characteristics or width of the response curve, said limiting means comprising a slot-like aperture stop (24).

7. The apparatus as claimed in claim 6, characterized in that the aperture stop (24) bounds a gap (25) extending diametrically over the ultrasonic transmitter (18) and running in the direction of the tear-off strip (11) thread.

8. A method for manufacturing blanks with a tear-off strip (11) or a tear-off thread for the purpose of wrapping packs (10), with the tear-off strip (11) or a tear-off thread being laid continuously on a continuously conveyed material web (12) and joined to the material web, and with blanks being then severed from the material web (12), comprising the following steps:

after the tear-off strip (11) has been laid on the material web (12), moving the material web past sensors which detect the tear-off strip (11) or the tear-off thread, the sensors being an ultrasonic transmitter (18) and an ultrasonic receiver (19) which are positioned on different sides of the material web (12), positioning the ultrasonic transmitter (18) and the ultrasonic receiver (19) such that the material web (12) conveyed between ultrasonic transmitter (18) and ultrasonic receiver (19) is registered by ultrasonic waves substantially exclusively in a region of the tear-off strip (11) or tear-off thread, constructing the ultrasonic transmitter (18) in such a way that a lobe or response curve generated by the ultrasonic transmitter corresponds approximately to a width of the tear-off strip (11), and connecting the ultrasonic receiver (19) to an evaluation unit which reacts to changes in intensity of the ultrasonic waves picked up by the ultrasonic receiver.

9. An apparatus for manufacturing blanks with a tear-off strip (11) or a tear-off thread for the wrapping of packs, with a continuous tear-off strip (11) or tear-off thread being laid on a continuously conveyed material web (12) in a region of a joining station and joined to the material web, so that blanks can be severed from the material web, said apparatus comprising:
a) following the joining station for applying the continuous tear-off strip (11) or thread to the material web (12), a testing device, for detecting the tear-off strip (11) or thread, positioned in a fixed location, and
b) means for moving the material web (12) past the testing device,
c) wherein the testing device comprises at least one ultrasonic transmitter (18) and at least one ultrasonic receiver (19) which are positioned on opposite sides of the material web (12), and
d) wherein said ultrasonic transmitter (18) and said ultrasonic receiver (19) are positioned in a region of the tear-off strip (11) or thread in such a way that ultrasonic waves, originating from the ultrasonic transmitter (18), strike the material web (12) substantially exclusively in a region of the tear-off strip (11) or thread, so that ultrasonic waves passing through the material web are picked up by the opposite ultrasonic receiver (19).

10. The apparatus as claimed in claim 9, characterized in that said ultrasonic transmitter (18) and said ultrasonic receiver (19) are positioned in a region of an upright section (20) of the material web (12), immediately above an upright suction belt (22) of a blank-cutting unit (16).

11. The apparatus as claimed in claim 9, characterized in that said ultrasonic transmitter (18) and said ultrasonic receiver (19) are oriented in an oblique position with respect to a plane of the material web (12).

12. The apparatus as claimed in claim 9, characterized in that the ultrasonic transmitter (18) is arranged underneath the ultrasonic receiver (19).

13. The apparatus as claimed in claim 9, characterized in that the ultrasonic transmitter (18) is provided with a limiting means on an outlet side thereof in order to influence the characteristics or width of the response curve, said limiting means comprising a slot-like aperture stop (24).

14. The apparatus as claimed in claim 13, characterized in that the aperture stop (24) bounds a gap (25) extending diametrically over the ultrasonic transmitter (18) and running in the direction of the tear-off strip (11) or thread.

* * * * *